United States Patent [19]
Reynolds et al.

[11] Patent Number: 5,130,123
[45] Date of Patent: Jul. 14, 1992

[54] DENTIFRICE

[75] Inventors: Eric C. Reynolds; Elsdon Storey; Wallace A. McDougall, all of Parkville, Australia

[73] Assignees: The University of Melbourne; The Victorian Dairy Industry Authority, Victoria, Australia

[21] Appl. No.: 145,034

[22] Filed: Jan. 19, 1988

Related U.S. Application Data

[63] Continuation-in-part of Ser. No. 624,087, Jun. 25, 1984, abandoned, which is a continuation-in-part of Ser. No. 441,528, Nov. 2, 1982, abandoned.

[30] Foreign Application Priority Data

Mar. 4, 1981 [AU] Australia ............................... PE7855
Jun. 23, 1981 [AU] Australia ............................... PE9429
Dec. 22, 1983 [AU] Australia ............................... PE2945

[51] Int. Cl.$^5$ ...................... A61K 7/16; A61K 37/16; A23J 1/20; C07K 3/00
[52] U.S. Cl. ...................................... 424/49; 530/360; 530/382
[58] Field of Search ................... 530/360, 382; 424/49

[56] References Cited

FOREIGN PATENT DOCUMENTS 825115 12/1959 United Kingdom ................. 424/54

OTHER PUBLICATIONS

Huxley, "Cariogenicity in Rats of a Diet Containing Lactalbumin or Casein as the Protein Source" *J. Dent Res* 56(8):900 Aug. 1977

Hackh's Chemical Dictionary, Fourth Edition, p. 137, 1972.

*Primary Examiner*—Nathan M. Nutter
*Attorney, Agent, or Firm*—Scully, Scott, Murphy & Presser

[57] ABSTRACT

A dentifrice composition useful in inhibiting caries and ginivitis comprising a caries and gingivitis inhibiting amount of a material selected from the group consisting of a water soluble salt of a whole caseinate, a water soluble salt of alpha$_s$-caseinate, a water soluble salt of beta-casinate and a digest of a whole caseinate, alpha$_s$-caseinate or beta-caseinate and mixtures thereof is disclosed.

20 Claims, No Drawings

DENTIFRICE

This is a continuation-in-part of U.S. patent application, Ser. No. 624,087 filed Jun. 25, 1984 and now abandoned which is a continuation-in-part of U.S. patent application, Ser. No. 441,528 filed Nov. 2, 1982 now abandoned.

This invention relates to caries inhibition. The invention also relates to gingivitis inhibition.

The present invention provides a dentifrice composition comprising a caries and gingivitis inhibiting amount of a material selected from the group consisting of a water soluble salt of a whole caseinate, a water soluble salt of alpha$_s$-caseinate, a water soluble salt of beta-caseinate and a digest of a whole caseinate, alpha$_s$-caseinate or beta-caseinate and mixtures thereof.

Preferably, said material comprises a water soluble salt which is substantially pure.

Preferably, said material is one exhibiting a reduction in calcium dissolution rate of at least 45 nmol/min. under the test conditions defined herein.

Preferably, said material is one exhibiting a reduction in calcium dissolution rate of at least 80 nmol/min. under the test conditions defined herein.

Preferably, said material is one exhibiting a reduction in calcium dissolution rate of at least 90 nmol/min. under the test conditions defined herein.

Preferably, said material is one exhibiting a reduction in calcium dissolution rate of at least 95 nmol/min. under the test conditions defined herein.

Preferably said material is selected from the group consisting of a water soluble alpha$_s$-caseinate, a water soluble beta-caseinate and a water soluble whole caseinate.

The solubility of the caseinates can be increased if they are digested. Such digestion can be effected chemically or proteolytically.

Preferred agents for digesting the caseinates are the protease such as trypsin, pepsin, chymotrypsin or pronase.

Applicants state that casein in milk may exist inter alia as a caseinate but if this be correct it is to be particularly noted that casein in milk is present in a micellar, water insoluble form in which it is in colloidal solution.

Accordingly the expression water soluble excludes caseinate in the form in which it may be present in milk.

Preferably, said material is present in said composition in solution.

Preferably, said material is present as 0.5 to 10 per cent by weight.

Preferably, said material is present as 0.5 to 5 per cent by weight.

Preferably, said material is present as 0.5 to 2 per cent by weight.

Preferably, said material is present as 0.5 to 1 per cent by weight.

The dentifrice may be a toothpaste or a tooth powder.

Alpha$_s$-caseinate and beta-caseinate are obtainable from milk.

The present invention provides the following procedures for selecting among the materials that may be used those that are most effective.

TEST 1

The purpose of this test is to determine hydroxyapatite dissolution and in this respect since tooth enamel is largely composed of hydroxyapatite it is believed that useful comparisons can be made.

Double distilled, deionised water (greater than 10 omega M/cm) was used throughout. Analytical reagent grade chemicals were obtained from Ajax Chemicals, Australia. Hydroxyapatite-spheroidal was purchased from BDH. The milk proteins obtained as sodium caseinate were fractionated by the method of Zittle and Custer (1), and their purity assessed by polyacrylamide gel electrophoresis using a modification of the method of Groves and Kiddy (2).

METHODS

Hydroxyapatite Dissolution Rate Assay

A chromatography column (pharmacia K9/15) containing 1 g. of hydroxyapaptite beads was used for the demineralisation assay. Tris 5 mM, pH 8.3 containing 50 mM NaCl and 20 mg/l neomycin was used as the column influent buffer at 20° C. and at a rate of 1.000±0.003 ml./min. A protein solution (10 mg. of protein in 10 ml. of influent buffer) was applied to the column and 1 ml. fractions were collected before and after protein application and assayed for total calcium, phosphate and protein. From these values a rate of dissolution (nmol calcium or phosphate per min) for each 1 ml fraction was obtained.

Calcium, Phosphate and Protein Assays

Inorganic phosphate was measured by the method of Itaya and Ui (3) and protein by the method of Bradford (4). The determination of calcium was by atomic absorption spectrophotometry using 1% lanthanum chloride to prevent phosphate suppression.

RESULTS

The proteins used for the study are listed in Table 1, they are all as water soluble salts and include four phosphoproteins and three non-phosphorylated proteins from the whey fraction of bovine milk. The effect of the individual proteins on hydroxyapatite dissolution rate is shown in Table 2.

TABLE 1

Properties of various water soluble salts of phosphorylated and non-phosphorylated acidic proteins.

| Protein: | Molecular weight | Phosphoserine Content[a] | Isoelectric Point | Carbohydrate Content |
|---|---|---|---|---|
| Phosvitin | 35,500 | 110 | 1.5 | + |
| sodium alpha$_s$-Caseinate | 23,613 | 8 | 4.1 | — |
| sodium beta-Caseinate | 24,020 | 5 | 4.5 | — |
| sodium kappa-Caseinate | 19,037 | 1 | 3.7 | + |
| alpha-lactalbumin | 14,174 | — | 5.1 | — |
| beta-lactoglobulin | 18,362 | — | 5.3 | — |
| Bovine serum albumin | 66,210 | — | 4.7 | — |

TD-casein (a tryptic digest of whole caseinate containing alpha$_s$, beta- and kappa-caseinates.
[a]Residues per mol protein

TABLE 2
Effect of phosphorylated and non-phosphorylated proteins on hydroxyapatite dissolution rate.

| Protein | Reduction in calcium dissolution rate[a] (nmol/min) | Reduction in phosphate dissolution rate (nmol/min) | Amount of protein bound (mg) |
|---|---|---|---|
| TD-caseinate | 109.2 ± 3.2[b] | 67.4 ± 5.6 | N.D. |
| sodium alpha$_s$-Caseinate | 100.1 ± 4.1[b] | 63.5 ± 3.3 | 5.58 ± 0.03 |
| sodium beta-Caseinate | 94.8 ± 11.7[b] | 64.0 ± 19.3 | 7.45 ± 0.37 |
| sodium kappa-Caseinate | 56.3 ± 8.9 | 33.7 ± 6.8 | 4.17 ± 0.26 |
| alpha-lactalbumin | 2.7 ± 1.7 | 2.9 ± 0.6 | 0.48 ± 0.17 |
| beta-lactoglobulin | 17.1 ± 1.7 | 12.5 ± 1.2 | 1.80 ± 0.71 |
| Bovine serum albumin | 31.6 ± 4.5 | 20.5 ± 3.3 | 2.09 ± 0.05 |

[a]means ±SD, n = 3
[b]not significantly different $P > 0.5$

In a trial of the above test the dissolution rate of hydroxyapatite as measured by the rate of calcium and phosphate released from the hydroxyapatite column was constant over a two hour period calcium 353.6±3.9 nmol/min, phosphate 225.4±6.8 nmol/min. The dissolution rates obtained using different hydroxyapatite columns showed greater variation, calcium 354.2±23.8 nmol/min, phosphate 229.6±30.8 nmol/min, n=11. This intercolumn variation in dissolution rate could be attributable to different column packing resulting in a different HA surface area exposed.

The mean differences between the steady-state dissolution rates before and after protein application, together with the amount of water soluble salt of protein bound, for all water soluble salts of proteins tested is presented in Table 2 above. The results show that the alpha$_s$-caseinate and beta-caseinate gave a marked reduction in the steady-state dissolution rate of HA with alpha$_s$-caseinate and beta caseinate both giving the same reduction in calcium and phosphate dissolution.

The results show that all the acidic proteins caused a reduction in the steady-state dissolution rate of hydroxyapatite. However, the greatest reduction was given by alpha$_{a}$-caseinate, beta-caseinate and to a lesser extent kappa-caseinate.

From the above and from other data which suggests that adjacent phosphate groups of water soluble salts of polyphosphoserine compounds have a spacing of about 6.88 Angstrom units which in a beta-pleated sheet configuration and that calcium atoms in a hydroxyapatite surface along the c-axis will also be spaced at about 6.88 Angstrom units, we speculate that a phosphate group-calcium atom bond materially reduces hydroxyapatite dissolution. References:

1. Zittle, C. A., Custer, J. H.: Purification and some properties of alpha$_s$-casein, J. Dairy Sci 46: 1183–1189, 1963,.
2. Groves, M. L., Kiddy, C. A.: Polymorphism of gamma-casein in cow's milk. Arch. Biochem. Biophys 126: 188–193, 1968.
3. Itaya, K., Ui, M.: A new micromethod for the colorimetric determination of inorganic phosphate. Clin. Chim, Acta 14: 361–366, 1966.
4. Bradford, M. M.: A rapid and sensitive method for the quantitation of microgram quantities of protein utilizing the principle of protein-dye binding. Anal. Biochem. 72: 248–254, 1976.

TEST 2

For the purpose of in vitro testing, the following test procedure for determining the effect of caseinates and whey protein on caries incidence in the Sprague-Dawley rat. Materials and Methods.

Forty-five, weanling, male Sprague-Dawley rats, 18 days old, bred from animals fed a fluoride free diet were used. The rats were marked for identification and then randomly distributed with respect to diet. They were housed in raised-bottom stainless-steel cages, one group of 15 per cage and fed a powdered cariogenic diet with either deionised water (control), a 2% alpha$_s$-caseinate solution or a 2% whey protein solution ad libitum. The cariogenic diet was a modified MIT—200 diet shown in Table 3.

TABLE 3

| Composition of modified MIT - 200 cariogenic diet. | |
|---|---|
| Component | % wt |
| Sucrose[a] | 67 |
| Wheyprotein Concentrate | 20 |
| Salt mixture[b] | 3 |
| Cottonseed oil | 3 |
| Cellulose[a] | 6 |
| Vitamin mixture[a,b] | 1 |

[a]Calcium and phosphate not detectable, fluoride content of complete diet was less than 0.2 g per g dry weight.
[b]Vitamin and Salt mixture described in detail elsewhere.

The animals were weighed daily and the amounts of powdered diet and liquid consumed over a 24 h period by each group was measured. After 42 days on the diet, the animals were killed by cervical dislocation and treated as described below.

Caries evaluation

Fissure caries was assessed using the method of Konig, Marthaler and Muhlemann (1958)(5). The mandible was removed from each rat and placed in formol-saline. The jaws were then sectioned and stained by the method of Konig et al (1958)(5), as described by Green and Hartles (1966)(6) to provide series of 100 micron thick longitudinal mesio-distal sections of the molar teeth. Only the main fissures of the first and second molar teeth were assessed for caries.

RESULTS

Diet Consumption

The relative consumption of solid and liquid diet by the three groups of rats was tested by an analysis of variance (by diet). This showed that the quantities of both solid and liquid consumed by each group were not significantly different ($P > 0.75$).

Caries analysis

The caries data shown in Table 4 were analysed in an analysis of variance table by diet.

TABLE 4

| | Caries Experience Data | |
|---|---|---|
| Animals | Carious fissures[a] | Smooth Surface caries |
| Control Group | 7.92 ± 2.06 (8.0 ± 2.0) | 11.7 ± 3.2 |
| Caseinate Group | 1.87 ± 2.50 (1.3 ± 1.6) | 2.3 ± 1.5 |

TABLE 4-continued

| Animals | Caries Experience Data | |
|---|---|---|
| | Carious fissures[a] | Smooth Surface caries |
| Whey Protein Group | 4.73 ± 3.85 (4.0 ± 3.1) | 11.3 ± 1.5 |

[a]Maximum number possible 10.

The animals drinking the 2% alpha$_{s1}$-caseinate solution had less carious fissures than the control animals ($p<0.001$), and the animals consuming the 2% whey protein solution had 40.3% less carious fissures than the control group ($p<0.01$). The correlation of caries incidence with the final weight of the rat was tested for the three groups. No correlation attained significance ($p>0.1$).

Similarly, the initial and final weights showed no correlation, nor were weight gain and caries incidence correlated.

CONCLUSION

Water soluble caseinates in the drinking water substantially reduced caries incidence of male Sprague-Dawley rats.

REFERENCES

5. Konig K. G., Marthaler T. M. and Muhlemann H. R. 1958: Methodik der Kurzfristig erzeugten Rattenkaries. Dr. Zahn-Mund-u. Kieferheilk. 29, 99–127.
6. Green R. M. and Hartles R. L. 1966; The effect of differing high carbohydrates diets on dental caries in the albino rat. Br. J. Nutr. 20, 317–323.

TEST 3

This test was to determine the effect of water soluble salts of protein on the adsorption of the bacterium *Streptococcus mutans* to hydroxyapatite.

MATERIALS AND METHODS

Hydroxyapatite discs were prepared by pressing 150 mg of hydroxyapatite (Bio-Gel HTP, Biorad Laboratores) for 5 min under 5 tons of pressure in a KBr press. The discs were hydrated then incubated with either various water soluble salts of protein solutions or imidazole buffer (0.05M pH 7.0, containing 0.025M NaCl). The adherence of $^3$H-labelled *S. mutans* PK1 cells was studied by incubating the pretreated discs with $^3$H-thymidine labelled cells ($10^9$ cells/ml) suspended in the imidazole buffer. The protein solutions used were all 5 mg/ml in imidazole buffer. The proteins and polypeptides studied were alpha$_s$-caseinate, beta-caseinate, kappa-caseinate, histone III, histone VIII, poly-1-lysine. The caseinates were prepared by selective precipitation from sodium caseinate and the other proteins were purchased from Sigma Chemical Co., Missouri, U.S.A.

RESULTS

The effect of pretreating hydroxyapatite discs with various protein solutions on the adherence of S. mutans cells is shown in Table 5.

TABLE 5

Effect of water soluble salts of protein on S. mutans adherence to hydroxyapatite.

| Proteins | Type | Number of S. mutans cells adsorbed (× $10^7$) |
|---|---|---|
| Control | — | 1.9 ± 0.6[a] |
| TD-caseinate[b] | acidic phosphoprotein digest | 0.5 ± 0.2 |
| sodium alpha$_{s1}$-caseinate | acidic phosphoprotein | 0.5 ± 0.3 |
| sodium beta-caseinate | acidic phosphoprotein | 0.4 ± 0.4 |
| sodium kappa-caseinate | acidic phosphoprotein | 0.6 ± 0.1 |
| histone III | basic protein | 2.2 ± 0.9 |
| histone VIII | basic protein | 2.6 ± 0.9 |
| poly-lysine | basic protein | 3.8 ± 1.1 |

[b]TD-caseinate-tryptic digest of whole caseinate.

All the water soluble caseinate fractions caused a reduction in bacterial adherence to hydroxyapatite. However, the basic proteins and polypeptides either had no effect or enhanced bacterial adherence to hydroxyapatite.

This test was to determine the effect of a solution of alpha$_s$-caseinate and a tryptic digest of caseinate (TD-caseinate) on "caries-like" changes in enamel slabs worn intra-orally on a removable appliance. The intra-oral appliance used was a modification of that used by Ostrom and Koulourides (1976). The dacron gauze was omitted and the two enamel slabs were placed with the labial surfaces facing each other approximately 0.5 mm apart in order to simulate an interproximal area. This produced a space 0.5×3×3 mm$^3$ between the two enamel slabs which allowed plaque accumulation. The appliances were worn for two weeks. Eight times a day the appliances were removed and placed in solutions at 37° C. for 10 min. The left side of the appliance was placed in a solution of 2% (w/v) sucrose, 2% (w/v) glucose, 140 mM KCl, 100 mM CaCl$_2$, 20 mM NaCl and pH 7.0, the right side was placed in either 2% (w/v) calcium alpha$_s$-caseinate or 2% (w/v) TD-caseinate in a solution of 2% (w/v) sucrose, 2% (w/v) glucose, 140 mM KCl, 100 mM CaCl$_2$, 20 mM NaCl and pH 7.0. At the completion of the experiment the enamel slabs were removed sectioned and subjected to microradiography and microhardness testing. The microradiography showed that the slabs exposed to the sugar-salt solution (left-side) had sub-surface, "caries-like" lesions. However, the slabs exposed to the sugar-salt solution containing either caseinate or TD-caseinate (right side) showed no "caries-like" changes. The results were confirmed by microhardness analysis.

CONCLUSION

Calcium alpha$_s$-caseinate or a tryptic digest at 2% (w/v) will inhibit "caries-like" changes in enamel slabs in situ. Hence, with respect to calcium alpha$_s$-caseinate's relative insolubility it would be more expedient to use the tryptic digest as the later material is quite soluble and the active peptides remain intact on proteolytic treatment.

Reference: Ostrom, C. A. and Koulourides, T.: The intraoral cariogenicity test in young subjects. Caries Res., 10: 442–452, 1976.

Having regard to the successful results obtained from using the above tests Applicants have formulated various compositions in accordance with this invention as follows. In general, the compositions contain from 0.5–20% by weight of water soluble salts of caseinates.

In preparation of a typical dentifrice within the scope of this invention, the requisite water soluble salt of the selected protein or polypeptide are incorporated into dentifrice compositions in any suitable manner depending on whether a powder, paste or liquid preparation is to be produced. For this purpose appropriate preparations of surface-active agents, binders, flavouring materials and other excipients required to achieve the required form of dentifrice are added.

The invention is further illustrated by the following examples:

EXAMPLE 1

Toothpaste

A toothpaste was prepared having the following composition:

| | |
|---|---|
| Calcium alpha$_s$-caseinate | 5.0% by weight |
| Gum tragacanth | 1.0% by weight |
| Saccharin | 0.1% by weight |
| Glycerin (B.P.) | 20.0% by weight |
| Sodium lauryl sulphate | 1.0% by weight |
| Methyl parahydroxy benzoate | 0.1% by weight |
| Flavouring and colouring | 1.0% by weight |
| Dibasic calcium phosphate | 35.0% by weight |
| Water | 36.8% by weight |

EXAMPLE 2

Toothpaste

A preparation as set out in example 9 was repeated but with the addition of 2% sodium fluoride in a suitable form.

EXAMPLE 3

Toothpaste

A preparation as set out in example 1 was repeated but with the addition of 0.4% stannous fluoride in a suitable form.

EXAMPLE 4

Toothpaste

A preparation as set out in example 1 was repeated but with the addition of 0.1% mono sodium fluorophosphate in a suitable form.

EXAMPLE 5

Tooth powder

The following preparation was made:

| | |
|---|---|
| Calcium alpha$_s$-Caseinate | 5.0% by weight |
| Soluble saccharin | 0.1% by weight |
| Colour agent | Trace by weight |
| Dibasic calcium phosphate | 94.1% by weight |

EXAMPLE 6

Tooth powder

A preparation as set out in example 5 was made but with the addition of 1% mono sodium fluorophosphate in a suitable form.

EXAMPLE 7

Liquid dentifrice

A preparation was made consisting of:

| | |
|---|---|
| Sodium alginate | 1.5% by weight |
| Calcium alpha$_s$-caseinate | 5.0% by weight |
| Sodium lauryl sulphate | 1.0% by weight |
| Flavouring | Trace by weight |
| Colouring | Trace by weight |
| Water | 92.5% by weight |
| pH adjusted to 7.0 | |

EXAMPLE 8

Liquid dentifrice

As for example 15 but with 0.5% sodium fluoride added.

EXAMPLE 9

Mouthwash

The following preparation was made:

| | |
|---|---|
| Sodium alpha$_s$-caseinate | 2.0% by weight |
| Sodium fluoride | 0.5% by weight |
| Flavouring | Trace by weight |
| Colouring | Trace by weight |
| Water | 97.5% by weight |

In the above, calcium alpha$_s$-caseinate was used principally because of economics but in lieu sodium alpha$_s$-caseinate or other caseinate might be used.

EXAMPLE 10

Preparation of a tryptic digest of caseinate

An aqueous mixture containing 10 gm sodium alpha$_s$-caseinate, 200 mgm trypsin (trypsin TPCK obtained from Sigma Chemical Company, Missouri, U.S.A.) and 1 liter of a 100 mM ammonium bicarbonate buffered solution having a pH of 8.53 was prepared, kept at 37° C. for 2 hours and then subject to freeze drying under vacuum to remove the water and ammonium bicarbonate to produce a tryptic digest of caseinate as a dry powder.

The tryptic digest of caseinate was readily soluble in pure water and also in acidic solutions such as exist in carbonated beverages and fruit juice.

EXAMPLE 11

Examples 1 and 9 were repeated using an equal weight of the tryptic digest of caseinate in lieu of calcium alpha$_s$-caseinate.

The claims form part of the disclosure of this specification.

We claim:

1. A composition comprising between 0.5% and 20% by weight, based on the total weight of said composition, of a material selected from the group consisting of a water soluble salt of a whole caseinate, a water soluble salt of alpha$_s$-caseinate, a water soluble salt of beta-caseinate and a digest of a whole caseinate, alpha$_s$-caseinate or beta-caseinate and mixtures thereof.

2. A composition as claimed in claim 1, characterized in that said material is one exhibiting a reduction in calcium dissolution rate of at least 45 nmol/min. in a demineralising assay under demineralisation conditions.

3. A composition as claimed in claim 2, wherein said material is one exhibiting a reduction in calcium dissolution rate of at least 80 nmol/min. in a demineralising assay under demineralisation conditions.

4. A composition as claimed in claim 2, wherein said material is one exhibiting a reduction in calcium dissolution rate of at least 90 nmol/min. in a demineralising assay under demineralisation conditions.

5. A composition as claimed in claim 2, wherein said material is one exhibiting a reduction in calcium dissolution rate of at least 95 nmol/min. in a demineralisation assay under demineralising conditions.

6. A composition as claimed in claim 1, characterized in that said material is selected from the group consisting of a water soluble $alpha_s$-caseinate a water soluble beta-caseinate, and a water soluble whole caseinate.

7. A composition as claimed in claim 1, wherein said material comprises a water soluble $alpha_s$-caseinate.

8. A composition as claimed in claim 1, wherein said material comprises a water soluble beta-caseinate.

9. A composition as claimed in claim 1, wherein said material comprises a water soluble whole caseinate.

10. A composition as claimed in claim 1, wherein said material is a digest of a whole caseinate, $alpha_s$-caseinate or beta-caseinate.

11. A composition as claimed in claim 10, wherein said digest is a chemical or proteolytic digest.

12. A composition as claimed in claim 10, wherein said digest is a trypsin, pepsin, chymotrypsin or pronase digest.

13. A composition as claimed in claim 1, wherein said material is present in said composition in solution.

14. A composition as claimed in claim 1, wherein said material is present in said composition in an amount of from 0.5 per cent to 10 per cent by weight.

15. A composition as claimed in claim 1, wherein said material is present in said composition in an amount of from 0.5 per cent to 5 per cent by weight.

16. A composition as claimed in claim 1, wherein said material is present in said composition in an amount of from 0.5 per cent to 2 per cent by weight.

17. A composition as claimed in claim 1, in the form of a toothpowder.

18. A composition as claimed in claim 1, in the form of a toothpaste.

19. A process of inhibiting dental caries and/or tooth erosion and/or gingivitis comprising applying to the teeth a composition in accordance with claim 1.

20. A composition as claimed in claim 1, in the form of a liquid preparation.

* * * * *